United States Patent [19]

Stevens et al.

[11] Patent Number: 4,519,905

[45] Date of Patent: * May 28, 1985

[54] HIGH PERFORMANCE ANALYTICAL COLUMN FOR ANION DETERMINATION

[75] Inventors: Timothy S. Stevens; Martin A. Langhorst, both of Midland, Mich.

[73] Assignee: The Dow Chemical Company, Midland, Mich.

[ * ] Notice: The portion of the term of this patent subsequent to May 10, 2000 has been disclaimed.

[21] Appl. No.: 626,569

[22] Filed: Jul. 2, 1984

Related U.S. Application Data

[63] Continuation of Ser. No. 431,431, Sep. 30, 1982, abandoned, which is a continuation of Ser. No. 234,520, Feb. 17, 1981, abandoned.

[51] Int. Cl.³ .............................................. B01D 15/08
[52] U.S. Cl. ................................. 210/198.2; 210/635; 521/28
[58] Field of Search ...................... 210/635, 636, 198.2, 210/198.3, 659; 521/28

[56] References Cited

U.S. PATENT DOCUMENTS

| | | | |
|---|---|---|---|
| 2,875,162 | 2/1979 | Morris | 521/28 |
| 2,910,445 | 10/1959 | Mock et al. | 521/28 |
| 3,920,397 | 11/1975 | Small et al. | 210/656 |
| 3,966,596 | 6/1976 | Stevens et al. | 210/198.2 |
| 4,070,283 | 1/1978 | Kirkland | 210/656 |
| 4,101,460 | 7/1978 | Small et al. | 210/198.2 |
| 4,119,580 | 10/1978 | Smith Jr., et al. | 521/28 |
| 4,160,728 | 7/1979 | Kirkland et al. | 210/656 |
| 4,252,644 | 2/1981 | Small et al. | 210/656 |
| 4,252,905 | 2/1981 | Bass | 210/656 |
| 4,280,923 | 7/1981 | Small et al. | 210/656 X |

OTHER PUBLICATIONS

Allen Terrance, *Particle Size Measurement;* pp. 85-90 (1974).

Hansen and Gilbert, "Theoretical Study of Support Design for High-Speed Liquid and Ion Exchange Chromatography", *Journal of Chromatographic Science,* vol. 12, pp. 464-472, (1974).

*Liquid Chromatographic Product Guide,* p. 3, Bulletin No. 123, Whatman, Inc. (1977).

Rootare, H. M., "A Review of Mercury Prosimetry," *Advanced Experimental Techniques in Powder Metallurgy,* vol. 5, pp. 225-246, Plenum Press (New York-- London, 1970).

Snyder and Kirkland, *Introduction to Modern Liquid Chromatography,* Second Edition, pp. 169, 210-214, and 414-419, John Wiley & Sons, (1977).

Wheaton and Hatch, *Ion Exchange,* vol. 2, Chapter 6, J. Marinske, (1969).

*Primary Examiner*—John Adee
*Attorney, Agent, or Firm*—Burke M. Halldorson

[57] ABSTRACT

An improved chromatographic analytical column, the column containing a pellicular type (agglomerated) anion-exchange packing, comprising:

Component A, which comprises a pressure packed bed of substrate particles of insoluble synthetic resin, having cation-exchanging sites at least on their available surfaces, the Component A particles being of low porosity relative to Component B microparticles, described below, and Component B, derived by agglomerating microparticles of insoluble synthetic resin onto the pressure packed bed of Component A particles, the microparticles having a volume average diameter of less than about 1,500 and greater than about 50 Angstroms and having anion-exchanging sites, at least on their outer surfaces, which attract available cation sites of Component A, wherein the microparticles of Component B are attached as a monolayer to the available surfaces of the Component A particles.

58 Claims, 3 Drawing Figures

HIGH PERFORMANCE ANALYTICAL COLUMN FOR ANION DETERMINATION

This is a continuation of application Ser. No. 431,431, filed Sept. 30, 1982, which is a continuation of application Ser. No. 234,520, filed Feb. 17, 1981, both abandoned.

FIELD OF THE INVENTION

The invention relates to an improved high performance analytical column containing an anion-exchange chromatographic packing composition of the pellicular (agglomerated) type.

BACKGROUND OF THE INVENTION

Since the inception of Ion Chromatography (U.S. Pat. No. 3,920,397), the basic technology for the anion-exchanger used in the analytical column for anion determination has not changed. Microparticles of anion-exchanger (0.1 to 5μ) are agglomerated with macroparticles (5 to 100μ) of surface sulfonated or fully sulfonated styrene divinylbenzene copolymer to produce a low capacity "pellicular type" anion-exchanger (U.S. Pat. No. 4,101,460).

Improvements within this basic technology came with the use of monodisperse anion-exchange latex rather than the previously used ground anion-exchange resin (as described in the '460 patent), and by performing the agglomeration step in a polyvalent salt solution (U.S. Pat. No. 4,119,580). The use of monodisperse anion-exchange latex eliminated the problem of refining ground ion-exchange resin to obtain the desired size range, while agglomerating in a polyvalent salt solution resulted in a reproducible and dense deposition of microparticles due to the resulting suppression of the ionic repulsion forces between the microparticles.

State of the art anion exchangers of this type show a performance level in which baseline separation of fluoride, chloride, nitrite, phosphate, bromide, nitrate, and sulfate anions is achieved in about 20 minutes using a one-half meter column, e.g., as illustrated by the chromatogram of FIG. 3 of the '580 patent.

The calculated theoretical plate count (N) for the bromide ion in this separation is $N = \sim 650$, and for the sulfate ion, $N = \sim 500$, using Equation 1, below, and measuring retention time from the leading edge of the little retained fluoride peak to correct for column void volume effects:

$$N = T^2/W \times 16 = \text{theoretical plate count} \qquad \text{Equation 1}$$

where
T = retention time, in minutes
W = triangulated peak width at baseline, in minutes.

Plate counts of about 650 for a ½ meter column are considered quite low by current liquid chromatographic standards, but about as expected for a pellicular packing (Bulletin No. 123, Whatman Inc., *Liquid Chromatographic Product Guide*, page 3 (1977)). Today, most liquid chromatography is practiced using the "microparticulate" type of packing, based on 5–10μ porous silica particles, because of their superior efficiencies (sharper peaks). This results in faster analyses, better detection limits, and better separation of interferences. Plate counts of 2,000–10,000 per 250 mm are common for microparticulate packed columns. All other factors the same, a column with four times the plate count will result in a twofold improvement in resolution with peaks about twice as tall. Thus, performance can be linearly compared by comparing the square root of N.

Based strictly on efficiency criteria, a silica based column, such as Whatman's Particil-10-25 SAX (strong anion exchanger), would thus appear to be strongly preferred for use in anion analysis versus the current pellicular form of column. However, prior attempts to use silica based columns for this application frequently prove unsuccessful, due in part to serious dissolution problems.

SUMMARY OF THE INVENTION

The invention is an improved chromatographic analytical column, the column containing a pellicular type (agglomerated) anion-exchange packing, comprising:

Component A, which comprises a pressure packed bed of substrate particles of insoluble synthetic resin, having cation-exchanging sites at least on their available surfaces, the Component A particles being of low porosity relative to Component B microparticles, described below, and Component B, derived by agglomerating microparticles of insoluble synthetic resin onto the pressure packed bed of Component A particles, the microparticles having a volume average diameter of less than about 1,500 and greater than about 50 Angstroms and having anion-exchanging sites, at least on their outer surfaces, which attract available cation sites of Component A, wherein the microparticles of Component B are attached as a monolayer to the available surfaces of the Component A particles.

The analytical column of the invention has advantages over chromatographic anion-exchangers described in the prior art in that it provides high performance versus prior pellicular (agglomerated) anion-exchange resin based columns; and further in that it may be utilized in strongly basic media which cause silica substrates used in silica based columns to disintegrate.

DETAILED DESCRIPTION OF THE INVENTION

Figure 1:
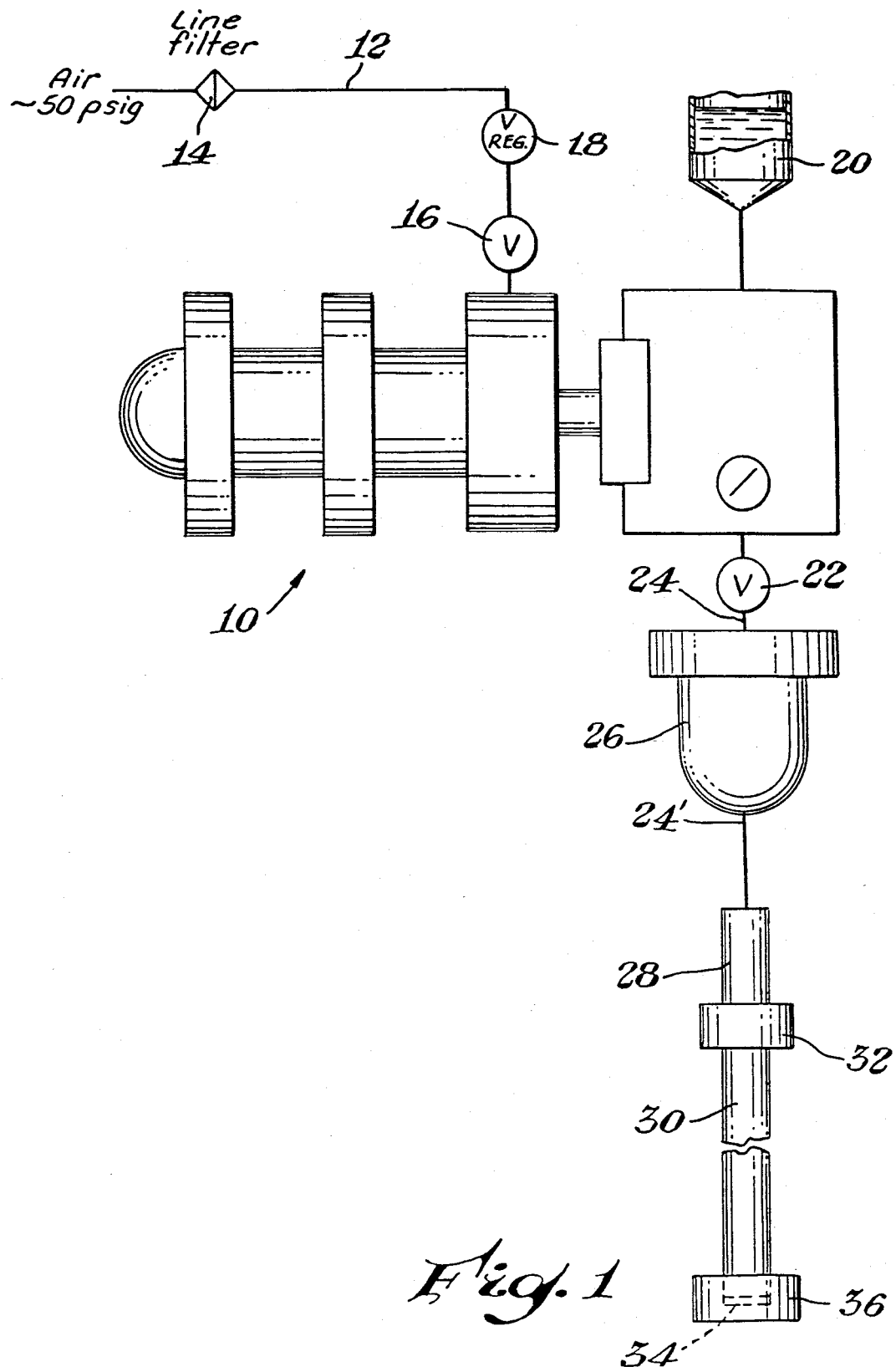
FIG. 1 is an elevational view of apparatus for preparing pressure packed chromatographic columns in accordance with the principles of this invention.

According to the present invention, low porosity substrate particles, typically resin beads, hereinafter Component A, serve to firmly retain coating microparticles (Component B monolayer) which include active anion-exchange sites used for chromatographic separation. Such substrate particles comprise synthetic resin insoluble in the solvent systems used for separation. They are suitably formed of resin beads preferably substantially spherical in shape of from about 5 to about 75 microns diameter and preferably about 5 to about 35 microns. Highly preferred for use in the invention are Component A particles which in diameter are from between about 5 to about 20 microns.

Preferred Component A is further characterized as being "monodisperse" meaning that at least about 90 percent and most preferably 95 percent of the particles which compose Component A are within the size range of about 0.5 to 1.5D, wherein (D) is the volume average diameter of the Component A particles. The narrower the size range of Component A, typically the more efficient the chromatographic packing composition of the invention. It is typically preferred to use Component A which meets the stricter requirement of a size range of between about 0.67 to 1.33D wherein 95 percent or greater of the Component A particles fall within this range.

The Component A particles have cation-exchange sites critically on their exterior or outer available surfaces. The cation-exchange sites may be either strong acid in form, generally of sulfonate functional groups; or weak acid in form, generally carboxyl functional groups. The term "cation-exchange sites" is in addition meant to include chelating sites, such as amino carboxylic acid groups, which are attracted to or form coordination complexes with the anion-exchanging sites of Component B.

A wide variety of condensation and addition backbone polymers are known in the art from which may be derived Component A. Examples of these synthetic resins and their preparation are amply described by Wheaton and Hatch in Chapter 6 of "Ion Exchange", Vol. 2, J. Marinsky Ed, New York (1969). For example, synthetic ion exchange resins such as poly(phenolformaldehyde), polyacrylic or polymethacrylic acid or nitrile, amine-epichlorohydrin resins, graft polymers of styrene on polyethylene or polypropylene, poly(2-chloromethyl-1,3-butadiene) and poly(vinyl aromatic) resins such as those derived from styrene, alpha-methylstyrene, chlorostyrene, chloromethylstyrene, vinyltoluene, vinylnaphthalene or vinylpyridine, all of which resins have been suitably cross-linked to render them insoluble in the solvent media with which they will be contacted and which bear desired cation exchanging sites, are suitable synthetic resins from which Component A may be prepared.

The preparation of resins with the mentioned chelating sites is also well known in the art, for example, as described by Morris, U.S. Pat. No. 2,875,162 (1959), and Mock et al., U.S. Pat. No. 2,910,445 (1959). Such a chelating resin, commercially available, is Dowex A-1 chelating resin.

Highly preferred for use as Component A, are the cross-linked poly(vinyl aromatic) resins. Especially suitable are synthetic resin beads of a styrene-divinylbenzene copolymer of the gel type containing about ½ percent or greater divinylbenzene (½%X), the beads being in the surface sulfonated form (such as by the sulfonating process described in U.S. Pat. No. 3,966,596); and containing about 20 percent or greater divinylbenzene (20%X) for a fully sulfonated form of bead particle.

As mentioned, Component A particles have low porosity relative to the Component B microparticles. "Low porosity" means that minute, discrete pores or channels (to be distinguished from irregular or undulating surface features) which permeate the interior of Component A, as in the case of macroreticular form resins, are insufficient in size to permeate substantial Component B microparticles during the agglomerating process. Low porosity resins particularly will include gel type resins; and selected macroreticular form resins having a volume average pore diameter ($D_p$) which is less than a factor of about three times greater than the volume average diameter (D) of the Component B microparticles combined therewith (i.e., the ratio $D_p/D$ is less than $\sim 3$).

The term "available surface", as used herein, means that surface of Component A which will come into attaching contact with microparticles of Component B when a pressure packed bed of Component A is contacted with a suspension of Component B microparticles. Because of the low porosity of Component A particles, the term available surface is thus equated with the outer surface area (external skin) of Component A, excluding substantially all minute internal pore created surface areas, (and which outer surface area is contacted by the suspension of Component B microparticles).

Monolayer

The packing used in the improved analytical column of the invention further comprises synthetic resin microparticles, hereinafter Component B, of less than about 1,500 and greater than about 50 Angstroms volume average diameter; a highly preferred form of which is further characterized as "monodisperse." The latter term, as applies to Component B, particularly refers to Component B microparticles of a volume average diameter (D), wherein no less than about 90 percent of the total volume of same is within the size range of between about 0.5D to about 1.5D. Monodisperse Component B particles (for illustrative purposes), of a volume average diameter of 500 Angstroms, would thus be composed of microparticles at least about 90 percent of the total volume of which would be within the size range of from about 250 to about 750 Angstroms. The defined microparticles of Component B form a monolayer on the available surface of Component A. These microparticles have anion-exchanging sites which attract the available sites of Component A.

The material from which the Component B microparticles are derived, again should be chosen so as to be insoluble in the solvents with which they will be contacted. Among suitable backbone materials for Component B are the well-known synthetic polymeric resins mentioned in the description of Component A above and may be of the gel or macroreticular resin type. Preferred for use in Component B are poly(vinyl aromatic) resins; most preferred is an aminated styrene-divinylbenzene copolymer (e.g., functionalized vinylbenzyl chloride-divinylbenzene) having anion-exchanging sites substantially throughout the entirety of a majority of the particles. The anion-exchanging sites are found at least on the outer surfaces of Component B particles, preferably substantially throughout the entirety of a majority of the particles. The anion-exchange sites may be either strong base, generally quaternary ammonium functional groups; or weak base, generally tertiary, secondary, and primary amine functional groups.

As mentioned above, Component B will comprise microparticles not greater than about 1,500 Angstroms volume average diameter. Preferably, the microparticles will be from about 50 to about 900 Angstroms, more preferably, from about 50 to about 600 Angstroms volume average diameter, and most preferably will be in the range of about 50 to about 300 Angstroms volume average diameter.

The term "volume average diameter" (D) as used herein to describe Component B is synonymous with the term "median diameter" appearing in U.S. Pat. No. 4,101,460. When referring to particle size, it relates to the statistical distribution of total particle volume with respect to varying particle size. One method used to determine the volume average diameter of microparticles involves determining the statistical median with respect to volume of the range of the particles' Martin's diameters present. The method is disclosed in U.S. Pat. No. 4,101,460 (particularly Col. 8, lines 32–44) for which teaching said patent is incorporated herein by reference.

For larger particles (Component A), "volume average diameter" may be determined, e.g., using a HIAC Particle Size Analyzer to supply a 12-channel number distribution over the range of the sensor. Particles in each channel are assumed to be spherical, and are assigned an average diameter corresponding to the midpoint of the two channel limits. Using the assigned diameters and the number distribution generated by the instrument, the volume average diameter is determined using the following equation:

$$\text{Vol. Avg. Diameter} = (\Sigma nd^{4*}/\Sigma nd^3)$$

where
n = number of particles in the channel
d = diameter of channel.

(*For a more detailed description, refer to "Particle Size Measurement", T. Allen, Chapman & Hall, 1974, pg. 85–90, incorporated herein by reference.)

The term "volume average pore diameter" ($D_p$) is a term well known in the art relating to the statistical distribution of total pore volume of the macroreticular resin with respect to varying pore diameter. The method employed herein for determining "volume average pore diameter" is the known technique of mercury porousimetry as described in "Advanced Experimental Techniques in Powder Metallurgy", Vol. 5, Plenum Press (1970).

The word "diameter" should not be construed as indicating that either Component A or Component B particles are exactly spherical in shape. Photomicrographs indicate the particles described in the Examples below are generally spherical. However, where Component B, for example, is formed from ground anion-exchange resin, projections, edges, or corners are very likely to be present due to the grinding process which may tend to shatter individual ion-exchange resin particles, producing irregular and diverse geometrically shaped particles, intended to be covered within the broad scope of the claimed invention.

Column Preparation and Apparatus

Analytical columns conforming to the invention are prepared by first efficiently pressure packing the column with Component A substrate particles, to which bed of packed Component A is added a suspension of Component B microparticles. "Pressure packing" means the technique, generally, of packing Component A which is characterized by: (1) delivery by liquid of a slurry or liquid suspension of Component A particles to a chromatographic column; and (2) wherein the delivery liquid is a packing liquid added to the column under high pressure (e.g., between about 200–10,000 psig) over a prolonged period, to form a generally homogenous packed bed of Component A, the bed being supported and built on a porous element or frit (which is permeable to the applied packing liquid).

Apparatus useful in preparing a pressure packed bed of Component A is illustrated in FIG. 1 and comprises a constant pressure pump designated by Reference Numeral 10 (suitably an air driven 2 H.P. pneumatic amplifier pump, Model No. 29266-1, Assembly No. DSTV-122-C, available from Haskel Engineering and Supply Company, Burbank, Calif.). The pump is operated from a compressed air tank through a pneumatic conduit 12, gas filter 14, shut-off valve 16, and gas pressure regulator 18, the latter of which controls the input pressure to pump 10.

Pump 10 is connected to a reservoir 20, from which packing liquid is withdrawn and delivered under controlled pressure through a shut-off valve 22 and tube segment 24 to a second reservoir or slurry reservoir 26 (such as available from Alltech Assoc., Inc., Chicago, Ill., Catalog No. 9501). A column extension or extension element 28 communicates with slurry reservoir 26 through a tube segment 24'. A chromatographic column 30 (the column to be packed) is removably coupled to column extension 28 by a chromatographic union 32. A frit 34 (suitably a porous stainless steel frit with a Kel-F ® perimeter ring from Beckman-Altex, Berkeley, Calif.) is inserted into the extreme lower end of column 30 and held by chromatographic end fitting 36. Suitably, the end fitting, column extension, and union used and described above, are standardized chromatograph parts, all available from Valco Instrument Company, Inc., Houston, Tex.

The apparatus is operated by adding to reservoir 26 a quantity of a batch prepared slurry of Component A, and prefilling column 30, column extension 28 and tube segments 24, 24' with packing liquid, making sure to displace all air from the system. Tube segment 24 is then coupled to pump 10, and the pump is operated to deliver packing liquid to the slurry reservoir and ultimately to column 30 at a controlled packing pressure over a prolonged period (e.g., at least about ½ hour). To avoid disrupting the bed following application of the packing liquid, valve 22 is closed, and with pump 10 so disengaged, the packing pressure is allowed to dissipate slowly, after which column 30 is detached and a column inlet frit and end fitting, identical to frit 34 and end fitting 36, attached. The packed bed is then rinsed thoroughly over repetitive periods with eluent to effect a clean-up. A liquid suspension of Component B is then contacted with the packed Component A bed using the in situ agglomeration method described in U.S. Pat. No. 4,101,460, whereby a monolayer of Component B is formed on the available surface of the pressure packed bed of Component A substrate particles.

Like the packing materials claimed in U.S. Pat. No. 4,101,460, the packing used in the improved columns of the present invention has been found to be remarkably stable. The particles of Component B are irreversibly attached to the available surface of Component A, such that a substantial number of Component B particles will not be displaced from the available surface of Component A by solutions of strong electrolytes or polyelectrolytes. For example, about 0.5 molar and preferably about 1.0 molar sodium hydroxide solution should not displace a substantial number of Component B particles; neither should shearing forces such as those encountered when a liquid passes through an ion-exchange bed at elevated flow rates displace a substantial number of Component B particles.

EXPERIMENTAL

Chromatograph Conditions

The following chromatographic conditions are used to evaluate the packed chromatographic columns described in the Examples, below.

Eluent: 0.0024M $Na_2CO_3$, 0.003M $NaHCO_3$
Flow Rate: 138 ml/hr
Stripper Column: 2.8×300 mm DOWEX 50 W×16, $H^+$ ion form resin, 200–400 mesh
Injection Volume: 50 $\mu$l loop
Detection: 7.5 $\mu$mho $cm^{-1}$ full chart deflection.

Sample Standard

The following seven-ion standard is used undiluted; as a 2× dilution; and also as a 4× dilution.

| | |
|---|---|
| $F^-$ | 3.3 ppm |
| $Cl^-$ | 4 ppm |
| $NO_{23}^-$ | 10 ppm |
| $PO_4^-$ | 54 ppm |
| $Br^-$ | 10 ppm |
| $NO_3^-$ | 34 ppm |
| $SO_4^-$ | 50 ppm |

The above conditions and standard solutions are widely used for the evaluation of Ion Chromatographic analytical columns (see U.S. Pat. No. 4,119,580).

Component B, Latex Synthesis

Component B is derived using the following recipe to synthesize a quaternized vinylbenzyl chloride divinylbenzene copolymer latex of a size of about 200 Angstroms volume average diameter. The use of more or less monomer results in larger or smaller latex; and reducing the charge of sodium persulfate, sodium bicarbonate, sodium lauryl sulfate, and sodium metabisulfite may be practiced to obtain larger sized latex, as is well understood in the art.

Recipe

1. Add 200 ml deionized water, 3 g sodium persulfate (Baker Grade, Baker Chemical Co.), 3 g sodium bicarbonate (Baker Analyzed Grade) and 35 g 30% aqueous solution of sodium lauryl sulfate (Alcolac Inc.) to a 500 ml round bottom flask, with mixing to dissolve the salts.

2. Place the flask on a rotary evaporator and rotate in an ice bath until a white slush forms (second phase sodium lauryl sulfate). Continue flask rotation to step 7.

3. Add 10 g of vinyl benzyl chloride monomer (VBC-XD1915.00, Dow Chemical Co.) and 1 g of 50% divinylbenzene monomer (DVB-55, Dow Chemical Co.) to the flask.

4. Add a solution of 2.1 g sodium metabisulfite (Baker Analyzed Grade) in 10 ml of deionized water to the flask.

5. Flush the headspace of the flask with nitrogen and cap the system to prevent the intrusion of air.

6. Replace the ice bath with a 32° C. water bath and maintain a 32° C. temperature for six hours.

7. Filter the resulting latex through Whatman #1 filter paper and add 2.5 g of Triton X-100 (Baker Chemical Co.) nonionic surfactant. Mix well.

8. Shake the above treated latex with 200 g of DOWEX MSA-1 ion exchange resin (Dow Chemical Co.) for 10 minutes to remove the sodium lauryl sulfate from solution. Filter on a 400 mesh stainless steel screen.

9. Shake the above treated latex with 200 g of DOWEX MR-3 mixed bed ion exchange resin (Dow Chemical Co.) for 10 minutes to demineralize the latex. Filter on a 400 mesh stainless steel screen (at this point, determining latex size).

10. Add 3 ml of 99% dimethyl ethanolamine (Aldrich Chemical Co.) to the above treated latex (to prepare Type 2 latex), mix and heat on a steam bath to 70±5° C. for one-half hour. Appropriately, substitute trimethylamine in this step and step 11 to prepare a Type 1 latex. (Type 1 latex being preferred for special use, e.g., to achieve a better separation of sulfate from oxalate).

11. Add 17 ml additional 99% dimethylethanolamine in 1 ml portions with mixing over a time span of about 15 minutes. Continue heating for 3 hours. Cool and filter through Whatman #1 filter paper.

12. Filter through a 0.45$\mu$ membrane filter and dilute to about 1% polymer solids with 10% sodium carbonate (Baker Analyzed Grade) prior to agglomerating the latex with Component A.

Column Packing

Pressure packed analytical columns in the Examples, below, are prepared using as the packing liquid, an aqueous solution of 0.002M $Na_2HPO_4$, to which is added a surfactant, suitably 0.2% (w/v) Brij 35 (polyoxyethylene (23) lauryl ether) from Aldrich Chemical Co., Inc., Milwaukee, Wis.; and additionally to which is added 0.05% (w/v) sodium lauryl sulfate and 0.2% formaldehyde; and adjusted to pH 7.5 by NaOH.

A slurry batch of Component A is prepared by adding 35% cross-linked, fully sulfonated styrene-divinylbenzene beads, 10–20$\mu$ particle size range, to the referenced packing liquid to produce a dilute slurry of approximately 20% solids content (v/v). The volume of the Component A used should approximate 2× the volume of the empty column 30. The prepared slurry batch is sonicated for at least 15 minutes to remove entrained gases prior to its addition to slurry reservoir 26.

Columns are each prepared using a packing pressure of about 2,000 psig, applied for at least ½ hour (for columns on the order of 10 cm, and correspondingly longer for longer columns) after which the pressure is allowed to dissipate slowly (preferably at least 4 hours) to avoid disrupting the packed Component A bed. The column is then detached from the packing apparatus, a frit and column end fitting installed, and the column is connected to a chromatographic pump to be rinsed with eluent for 3–4 hours, allowed to set overnight, and then rinsed an additional 3–4 hours.

Anion-exchange latex is agglomerated onto the available surface of the packed Component A bed by passing a 1% polymer solids (w/v) suspension of an anion-exchange latex in 10% (w/v) sodium carbonate through the column until an excess is seen emerging. The column is subsequently heated at 55° C. in a water bath to promote complete agglomeration followed by rinsing with 10% (w/v) sodium carbonate and finally by rinsing with the standard eluent solution.

EXAMPLE 1

Pressure packed chromatographic columns conforming to the invention are prepared by packing nonagglomerated Component A particles into 4.6×70 mm chromatographic columns. Component B in the form of 5% cross-linked Type 2 latex (hereinafter Type 2×5 latex) is agglomerated onto the packed Component A bed. Separate columns are prepared using latex of 535, 910 and 1,500 Angstroms, respectively, volume average diameter. None of these evaluated columns show an increase in back pressure after the in situ agglomeration step indicating that there is no column plugging. The observation is also made that the column using the 535 Å latex obtains about the same resolution of the seven-ion standard as the 910 Å latex column in about 40% less time (with even greater efficiency advantage observed when compared to the 1,500 Å latex column). This performance is contrary to generally accepted theory (Hansen and Gilbert "Theoretical Study of Support Design For High-Speed Liquid and Ion Exchange Chromatography"; Chrom. Sc., August, 1974, p. 464).

This theory of pellicular ion-exchangers is a modification of the Glueckauf equation whereby plate count and resolution are calculated as a function of pellicule depth (thickness of the active ion exchange on the inactive core). Based on this theory, Hansen and Gilbert calculated the optimum pellicule depth for various packing diameters and concluded that the pellicule depth should be about 12,000 Angstroms for a 50μ packing, about 3000 Angstroms for a 15μ packing, and about 1000 Angstroms for a 2μ packing (see Table II of this reference).

Figure 2:
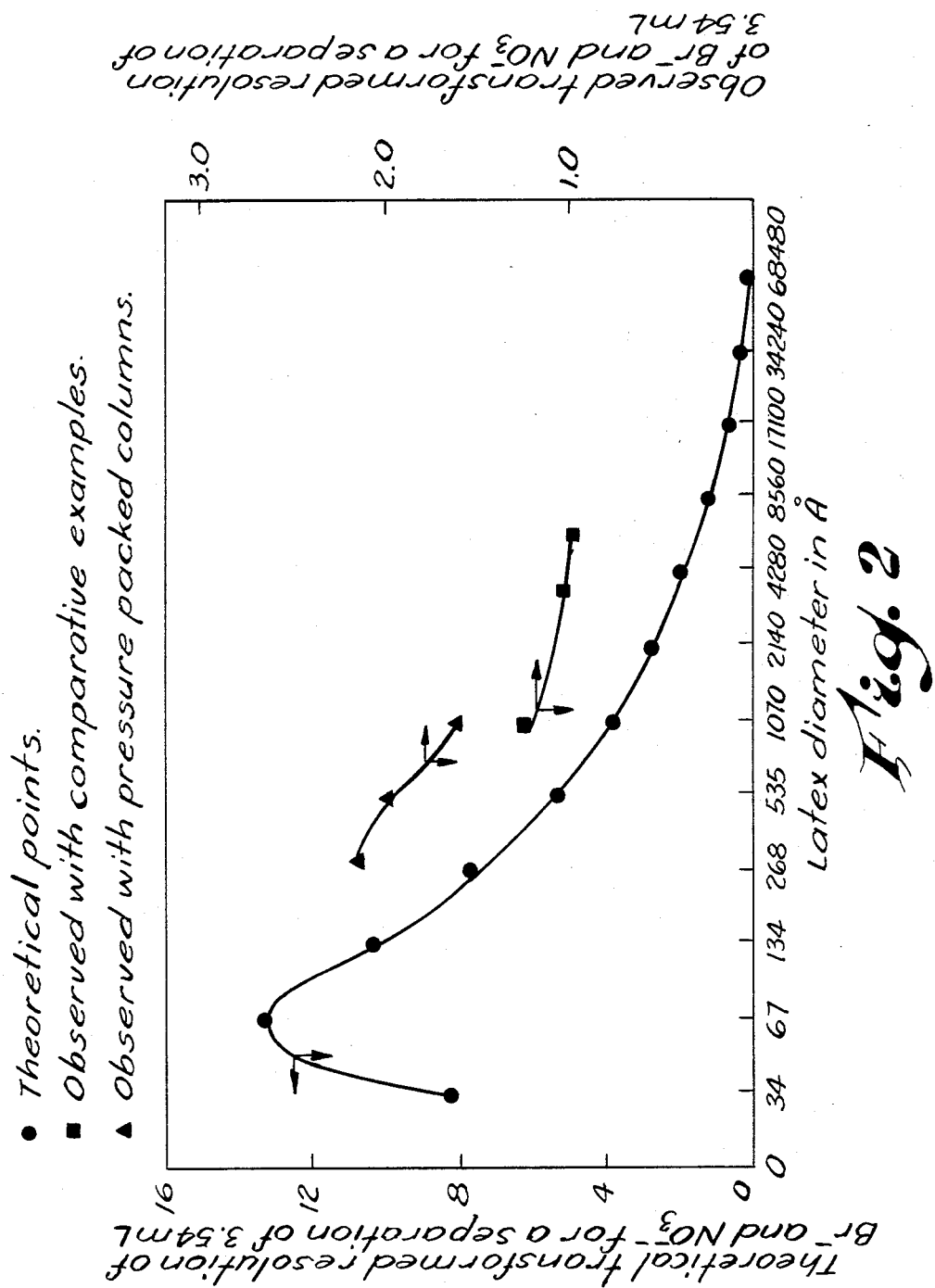
FIG. 2 is a graph which plots theoretically derived analytical column resolution performance, based on varying Component B size, and superimposed with the theoretically derived data are curves plotted based on observed performance, this data being associated with Examples 1 and 2, below.

Closer examination of Hansen and Gilbert's work, however, reveals a questionable assignment of variables. Their data is extrapolated from the boundary conditions of a fully functional packing (pellicule depth equal to the radius of the packing) to a packing having the "optimum" pellicule depth of only about 5% of the packing radius. Extrapolating over a very much shorter range based on the observed relative peak retention times ($K_d$) for bromide and nitrate with the agglomerated packing composed of 535 Angstroms Component B on a 10-20μ Component A substrate (using the herein stated eluent and eluent flow rate), the transformed resolution derived from Equation 3, below vs. pellicule depth curve shown in FIG. 2 results. The optimum theoretical Component B size based on these revisions is about 70 Angstroms as opposed to Gilbert and Hansen's predicted 3000 Angstroms. In addition, the curve of FIG. 2 shows surprisingly that optimum resolution should be expected in the range of from less than about 900 to about 50 Angstroms, a range unpredicted in the prior referenced patent and literature teachings.

EXAMPLE 2

Comparison of Different Latex Sizes

In order to experimentally determine optimum Component B size, various pressure packed columns, differing in Component B latex size, are prepared and evaluated using the standard conditions. The resulting data is shown in Table I.

TABLE I

Comparison of Resolution Between Br⁻ and NO₃⁻ For Columns Prepared with Various Latex Sizes

| Latex agglomerated in situ with 10-20μ Substrate[b] | Column Size | Resolution[a] of Br⁻ & NO₃⁻ | Separation of Br⁻ NO₃⁻ |
|---|---|---|---|
| 270Å Type 2 × 5 | 10 × 80 mm | 2.10 | 3.45 ml |
| 535Å Type 2 × 5 | 4.6 × 70 mm | 0.77 | 0.58 ml |
| 910Å Type 2 × 5 | 4.6 × 70 mm | 0.81 | 0.93 ml |
| 3760Å Type 2 × 5* | 2.8 × 500 mm | 1.00 | 3.54 ml |

TABLE I-continued

Comparison of Resolution Between Br⁻ and NO₃⁻ For Columns Prepared with Various Latex Sizes

| Latex agglomerated in situ with 10-20μ Substrate[b] | Column Size | Resolution[a] of Br⁻ & NO₃⁻ | Separation of Br⁻ NO₃⁻ |
|---|---|---|---|
| 6250Å Type 2 × 5* | 2.8 × 75 mm | 1.14 | 5.3 ml |

*Comparative Example (column prepared by the claimed preagglomeration method of U.S. Pat. No. 4,119,580). 3760Å latex is on a 50μ substrate.

[a]Resolution, $R = \dfrac{S}{\frac{1}{2}(W_1 + W_2)}$ (Equation 2)

where S = separation, in ml, between peak maximas
W = triangulated peak width at baseline in ml
[b]Fully sulfonated 35% cross-linked styrene divinylbenzene copolymer.

Comparison of column performance is made on the basis of the resolution observed for a given analysis time under standard conditions of eluent composition and flow rate. A column that gives a resolution of 1 and requires an analysis time of 20 minutes is not considered to perform as well as one that takes 10 minutes to give a resolution of 1. In order to more equally evaluate the column performance shown in Table I, the resolutions observed are transformed to the resolution expected for a separation between Br⁻ and NO₃⁻ of 3.54 ml, using the following equation.

$$R_{TR} = Ro \dfrac{\sqrt{3.54}}{\sqrt{S}} \qquad \text{(Equation 3)}$$

where
ro = resolution observed at separation S
$R_{TR}$ = transformed resolution, expected at a separation of 3.54 ml.

Figure 3:
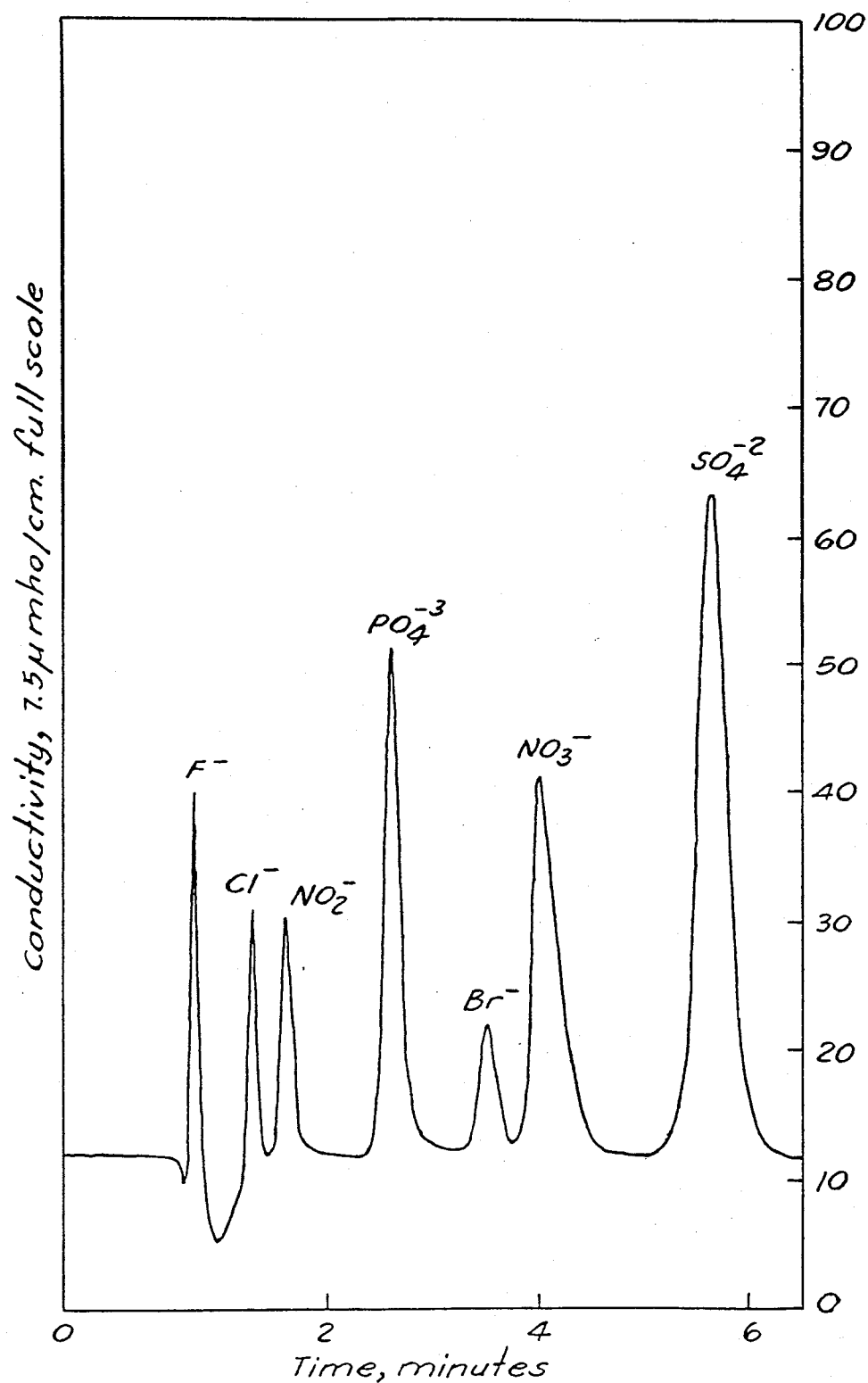
FIG. 3 reproduces an actual chromatogram developed by the improved high performance analytical column of this invention, and is particularly associated with Example 3, below.

The value of S = 3.54 ml is chosen as being the same as is seen with the prior art packing (FIG. 3, U.S. Pat. No. 4,119,580). Table II shows the transformed data.

TABLE II

Transformed Resolution for a Separation Between Nitrate and Bromide of 3.54 ml for Columns Prepared with Various Latex Sizes

| Latex Agglomerated in situ with 10-20μ Substrate | Resulting Column Size | Transformed Resolution of Br⁻ & NO₃⁻ | Resulting Separation of Br⁻ & NO₃⁻ |
|---|---|---|---|
| 270 Å Type 2 × 5 | 10 × 82 mm | 2.13 | 3.54 ml |
| 535 Å Type 2 × 5 | 4.6 × 427 mm | 1.90 | 3.54 ml |
| 910 Å Type 2 × 5 | 4.6 × 266 mm | 1.58 | 3.54 ml |
| 3760 Å Type 2 × 5* | 2.8 × 500 mm | 1.00 | 3.54 ml |
| 6250 Å Type 2 × 5* | 2.8 × 62 mm | 0.99 | 3.54 ml |

*Comparative Example.

The data in Table II is plotted with the theoretical curve for comparison, see FIG. 2. FIG. 2 also contains data for slurry packed column agglomerated in situ with 910 Å Type 2×5 latex (not considered prior art but included for comparative purposes). The observed performance, superimposed with the curve predicted by the revised theory, indicates agreement with the trend shown by the theoretical calculations. Performance is shown particularly to improve with the use of pressure packed columns vs. the other forms of columns such as those prepared according to U.S. Pat. No. 4,119,580. The most efficient columns are those prepared by pressure packing, and which additionally employed as Component B, smaller latex sizes in the range of from about 900 Angstroms to about 50 Angstroms.

EXAMPLE 3

Illustrative Chromatogram

A 4.6×140 mm column is pressure packed with fully sulfonated 10–20μ S-DVB (35%/X) Component A and agglomerated with 535 Å Type 2×5 latex as previously described. FIG. 3 shows a reproduction of the chromatogram developed by the column using the standard conditions and a 4X dilution of the seven-ion standard. The chromatogram compares very favorably with that reproduced as FIG. 3 of U.S. Pat. No. 4,119,580. Importantly, an analysis time of about 6 minutes is required for a near baseline resolution of the seven-ion standard. This compares with an analysis time of about 20 minutes with the referenced prior art chromatogram (FIG. 3 of U.S. Pat. No. 4,119,580) in which there was used the same eluent composition and eluent flow rate.

EXAMPLE 4

Column Geometry and Back Pressure

A disadvantage with the use of smaller packing size is increased back pressure. Most ion chromatographs are limited to a 500 psig maximum pressure and the 4.6 mm I.D. columns packed with fully sulfonated 10–20μ S-DVB(35%X) Component A gave back pressure well in excess of 500 psig for column lengths needed for a 10 or 20 minute analysis of the seven-ion standard (2× dilution). For example, the back pressure on a 4.6×430 mm column is about 2,000 psig. In order to reduce back pressure, a 10×100 mm pressure packed column is prepared according to the invention, having about the same column volume as the 4.6×430 mm column. This larger bore column shows a back pressure of only about 200 psig and results in near equivalent performance to the smaller bore column; i.e., a theoretical plate count according to Equation 1 of 3620 for the bromide ion peak and 2850 for the sulfate ion peak vs. respective values of 4000 and 3140 for the 4.6×430 mm column.

What is claimed is:

1. A chromatographic analytical column, the column containing a pellicular type (agglomerated) anion-exchange packing, comprising:
   Component A, which comprises a pressure packed bed of substrate particles of insoluble synthetic resin, having cation-exchanging sites at least on their available surfaces, the Component A particles being of low porosity relative to Component B microparticles, described below, and
   Component B, derived by agglomerating microparticles of insoluble synthetic resin onto the pressure packed bed of Component A particles, the microparticles having a volume average diameter of less than about 1000 Angstroms and greater than about 50 Angstroms and having anion-exchanging sites, at least on their outer surfaces, which attract available cation sites of Component A, wherein the microparticles of Component B are attached as a monolayer to the available surfaces of the Component A particles.

2. The analytical column of claim 1 in which the volume average diameter of the microparticles is not greater than about 900 Angstroms.

3. The analytical column of claim 2 in which the microparticles are monodisperse.

4. The analytical column of claim 1 comprising component A consisting essentially of monodisperse particles of insoluble synthetic resin of between about 5 to 75 microns diameter.

5. The analytical column of claim 4 comprising Component B consisting essentially of monodisperse microparticles of insoluble synthetic resin, the volume average of which is not greater than about 900 Angstroms.

6. The analytical column of claim 5 comprising Component A consisting essentially of insoluble synthetic resin particles of the gel type.

7. The analytical column of claim 4 in which the volume average diameter of the microparticles is from between about 50 to 600 Angstroms.

8. The analytical column of claim 7 comprising Component A consisting essentially of insoluble synthetic resin particles of the gel type.

9. The analytical column of claim 1 comprising Component A consisting essentially of monodisperse particles of insoluble synthetic resin of between about 5 to 35 microns diameter.

10. The analytical column of claim 9 comprising Component B consisting essentially of monodisperse microparticles of insoluble synthetic resin, the volume average diameter of which is between about 50 to 900 Angstroms.

11. The analytical column of claim 10 comprising Component A consisting essentially of insoluble synthetic resin particles of the gel type.

12. The analytical column of claim 9 comprising Component B consisting essentially of monodisperse microparticles of insoluble synthetic resin, the volume average diameter of which is from between about 50 to 600 Angstroms.

13. The analytical column of claim 12 comprising Component A consisting essentially of insoluble synthetic resin particles of the gel type.

14. The analytical column of claim 1 comprising Component A consisting essentially of monodisperse particles of insoluble synthetic resin of between about 5 to 20 microns diameter.

15. The analytical column of claim 14 comprising Component B consisting essentially of monodisperse microparticles of insoluble synthetic resin, the volume average diameter of which is between about 50 to 900 Angstroms.

16. The analytical column of claim 15 comprising Component A consisting essentially of insoluble synthetic resin particles of the gel type.

17. The analytical column of claim 15 in which the volume average diameter of the microparticles is not greater than about 600 Angstroms.

18. The analytical column of claim 17 comprising Component A consisting essentially of synthetic resin of the gel type.

19. The analytical column of claim 15 in which the volume average diameter of the microparticles is not greater than about 300 Angstroms.

20. The analytical column of claim 19 comprising Component A consisting essentially of synthetic resin of the gel type.

21. The analytical column of claim 1 comprising Component A consisting essentially of monodisperse particles of an insoluble sulfonated poly(vinyl aromatic) resin, and Component B consisting essentially of an insoluble aminated poly(vinyl aromatic) resin of latex derived monodisperse microparticles.

22. The analytical column of claim 21 in which the volume average diameter of the microparticles is not greater than about 900 Angstroms.

23. The analytical column of claim 22 comprising Component A consisting essentially of insoluble synthetic resin of the gel type.

24. The analytical column of claim 21 comprising Component A consisting essentially of particles of between about 5 to 75 microns diameter.

25. The analytical column of claim 24 in which the volume average diameter of the microparticles is from between about 50 to 900 Angstroms.

26. The analytical column of claim 25 comprising Component A consisting essentially of insoluble synthetic resin of the gel type.

27. The analytical column of claim 24 in which the volume average diameter of the microparticles is not greater than about 600 Angstroms.

28. The analytical column of claim 27 comprising Component A consisting essentially of synthetic resin of the gel type.

29. The analytical column of claim 24 in which the volume average diameter of the microparticles is not greater than about 300 Angstroms.

30. The analytical column of claim 29 comprising Component A consisting essentially of insoluble synthetic resin of the gel type.

31. The analytical column of claim 21 comprising Component A consisting essentially of particles of between about 5 to 35 microns diameter.

32. The analytical column of claim 31 in which the volume average diameter of the microparticles is from between about 50 to 900 Angstroms.

33. The analytical column of claim 32 comprising Component A consisting essentially of synthetic resin of the gel type.

34. The analytical column of claim 31 in which the volume average diameter of the microparticles is not greater than about 600 Angstroms.

35. The analytical column of claim 34 comprising Component A consisting essentially of synthetic resin of the gel type.

36. The analytical column of claim 31 in which the volume average diameter of the microparticles is not greater than about 300 Angstroms.

37. The analytical column of claim 36 comprising Component A consisting essentially of synthetic resin of the gel type.

38. The analytical column of claim 16 comprising Component A consisting essentially of particles of between about 5 to 20 microns diameter.

39. The analytical column of claim 36 in which the volume average diameter of the microparticles is from between about 50 to 300 Angstroms.

40. The analytical column of claim 39 comprising Component A consisting essentially of insoluble synthetic resin of the gel type.

41. The analytical column of claim 38 in which the volume average diameter of the microparticles is between about 50 to 600 Angstroms.

42. The analytical column of claim 41 comprising Component A consisting essentially of insoluble synthetic resin of the gel type.

43. The analytical column of claim 38 in which the volume average diameter of the microparticles is between about 50 to 300 Angstroms.

44. The analytical column of claim 43 comprising Component A consisting essentially of insoluble synthetic resin of the gel type.

45. The analytical column of claim 1 comprising Component A consisting essentially of monodisperse particles of an insoluble sulfonated styrene-divinylbenzene copolymer resin, and Component B consisting essentially of monodisperse microparticles of an insoluble quaternized vinylbenzylchloride-divinylbenzene copolymer latex derived resin having anion exchanging sites substantially throughout the entirety of a majority of the microparticles.

46. The analytical column of claim 45 comprising Component A consisting essentially of a gel form resin of said styrene-divinylbenzene copolymer.

47. The analytical column of claim 45 comprising Component A consisting essentially of particles of about 5 to 75 microns diameter, and Component B in which the volume average diameter of the microparticles is less than about 900 Angstroms.

48. The analytical column of claim 47 comprising Component A consisting essentially of a gel form resin of said styrene-divinylbenzene copolymer.

49. The analytical column of claim 45 comprising Component A consisting essentially of particles of about 5 to 35 microns diameter, and Component B in which the volume average diameter of the microparticles is from between about 50 to 900 Angstroms.

50. The analytical column of claim 49 comprising Component A consisting essentially of a gel form resin of said styrene-divinylbenzene copolymer.

51. The analytical column of claim 49 in which the volume average diameter of the microparticles is between about 50 to 600 Angstroms.

52. The analytical column of claim 51 comprising Component A consisting essentially of a gel form resin of said styrene-divinylbenzene copolymer.

53. The analytical column of claim 45 comprising Component A consisting essentially of particles of about 5 to 20 microns, and Component B in which the volume average diameter of the microparticles is between about 50 to 900 Angstroms.

54. The analytical column of claim 53 comprising Component A consisting essentially of a gel form resin of said styrene-divinylbenzene copolymer.

55. The analytical column of claim 53 in which the volume average diameter of the microparticles is between about 50 to 600 Angstroms.

56. The analytical column of claim 55 comprising Component A consisting essentially of a gel form resin of said styrene-divinylbenzene copolymer.

57. The analytical column of claim 53 in which the volume average diameter of the microparticles is between about 50 to 300 Angstroms.

58. The analytical column of claim 7 comprising Component A consisting essentially of a gel form resin of said styrene-divinylbenzene copolymer.

* * * * *

UNITED STATES PATENT AND TRADEMARK OFFICE
CERTIFICATE OF CORRECTION

PATENT NO. : 4,519,905
DATED : May 28, 1985
INVENTOR(S) : Stevens et al.

It is certified that error appears in the above—identified patent and that said Letters Patent is hereby corrected as shown below:

```
Column 6, line 34, delete "to".
Column 9, line 64, after "Br-" insert --&--.
Column 10, line 8, after "Br-" insert --&--.
          line 35, delete "ro" and insert --Ro--.
Column 13, line 52, delete "16" and insert --21--.
           line 55, delete "36" and insert --38--.
           line 57, delete "300" and insert --900--.
Column 14, line 61, delete "7" and insert --57--.
```

Signed and Sealed this

Twenty-fifth Day of February 1986

[SEAL]

*Attest:*

DONALD J. QUIGG

*Attesting Officer*    *Commissioner of Patents and Trademarks*